United States Patent
Clarkson et al.

(10) Patent No.: US 11,445,628 B1
(45) Date of Patent: Sep. 13, 2022

(54) PACKAGING TECHNIQUES FOR ELECTRONIC DEVICES

(71) Applicant: Verily Life Sciences LLC, South San Francisco, CA (US)

(72) Inventors: Jeff Clarkson, Richmond, CA (US); Roseann Ahlin, San Jose, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 335 days.

(21) Appl. No.: 16/395,375

(22) Filed: Apr. 26, 2019

Related U.S. Application Data

(60) Provisional application No. 62/663,888, filed on Apr. 27, 2018.

(51) Int. Cl.
　　 $H05K\ 5/06$ 　　 (2006.01)
　　 $H05K\ 5/00$ 　　 (2006.01)
　　 $A61B\ 5/145$ 　　(2006.01)

(52) U.S. Cl.
　　 CPC .......... $H05K\ 5/066$ (2013.01); $H05K\ 5/0095$ (2013.01); $A61B\ 5/14532$ (2013.01)

(58) Field of Classification Search
　　 CPC ... A61B 5/14532; H05K 5/0095; H05K 5/066
　　 See application file for complete search history.

(56) References Cited

U.S. PATENT DOCUMENTS

| | | | |
|---|---|---|---|
| 6,232,150 | B1 | 5/2001 | Lin et al. |
| 2007/0268581 | A1 | 11/2007 | Palmateer |

FOREIGN PATENT DOCUMENTS

WO　2018/074311　*　4/2018

OTHER PUBLICATIONS

Holt et al., "Fabrication and control of a microheater array for Microheater Array Powder Sintering", The International Journal of Advanced Manufacturing Technology 95.1 (2018): 1369-1376.
Lin , "Packaging Issues of MEMS Devices", University of California at Berkeley (2002).
Lin , "Packaging Schemes for MEMS", Packaging Course, University of California at Berkeley (2004).
Williams , "Packaging for MEMS", BSAC Seminar, Oct. 2000.

* cited by examiner

*Primary Examiner* — Carl J Arbes
(74) *Attorney, Agent, or Firm* — Kilpatrick Townsend & Stockton LLP

(57) ABSTRACT

One disclosed method includes defining an electrical trace on a first substrate; physically coupling an electronic component to the first substrate, wherein a portion of the electrical trace completely encircles the electronic component; overlaying a second substrate onto the first substrate, the overlaying causing the second substrate to completely cover the portion of the electrical trace and the electronic component; electrically coupling an electrical power source to the electrical trace to generate a current in the electrical trace; melting the second substrate using heat generated by the current through the electrical trace; and fusing the second substrate to the first substrate to generate a hermetic seal around the electronic component.

18 Claims, 16 Drawing Sheets

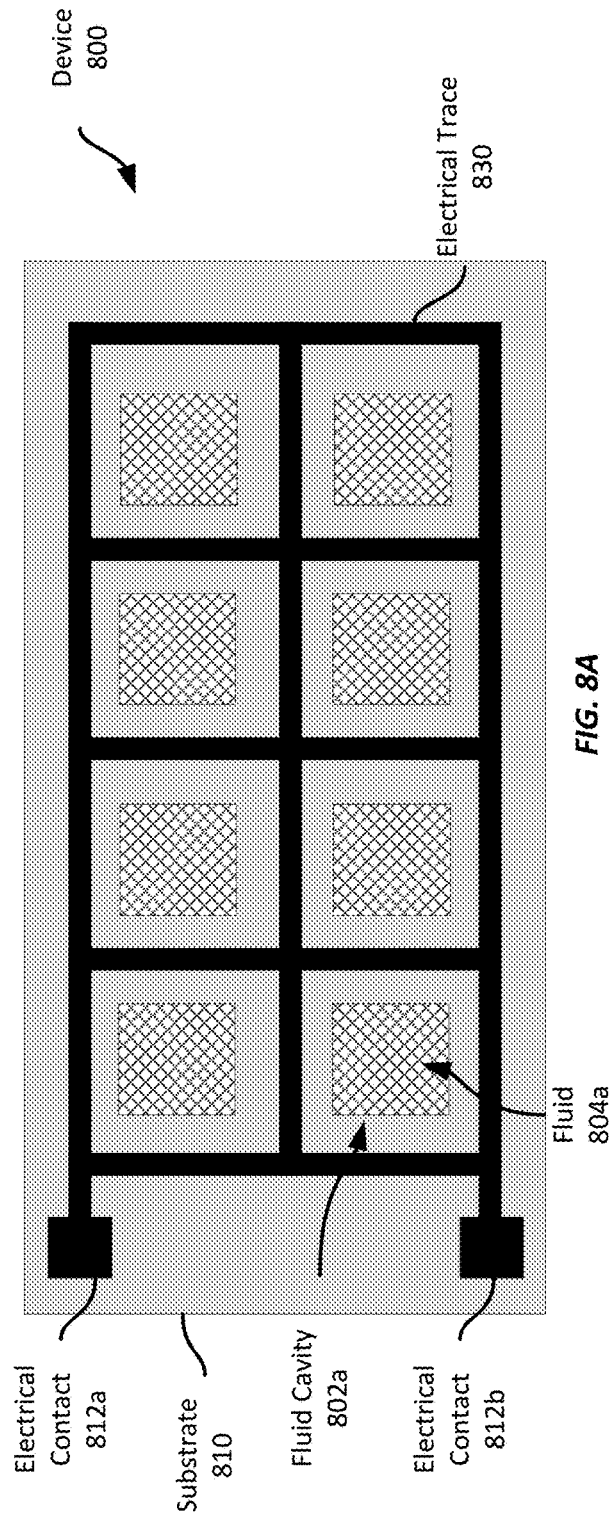 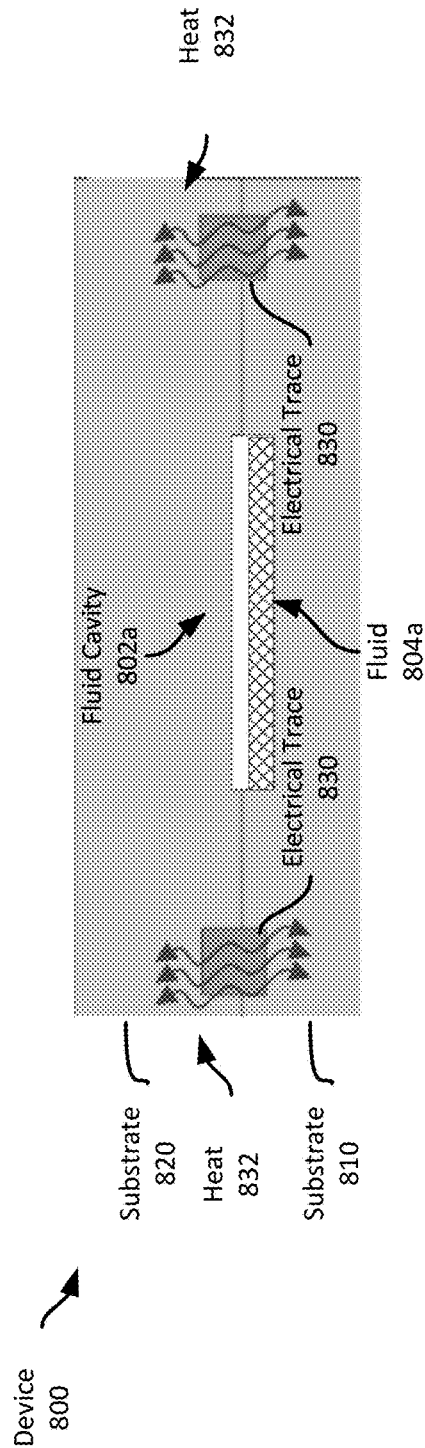
FIG. 8A
FIG. 8B

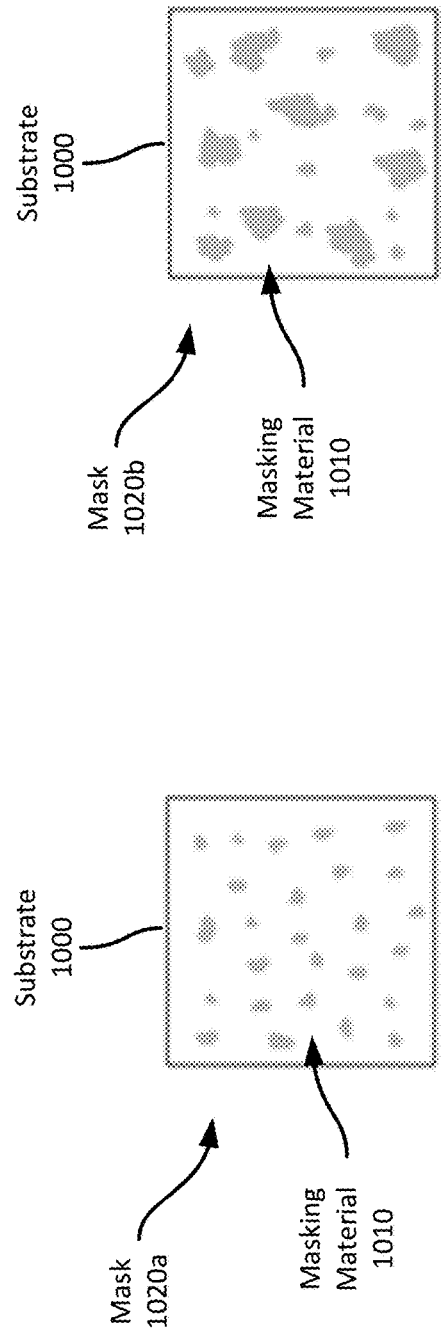
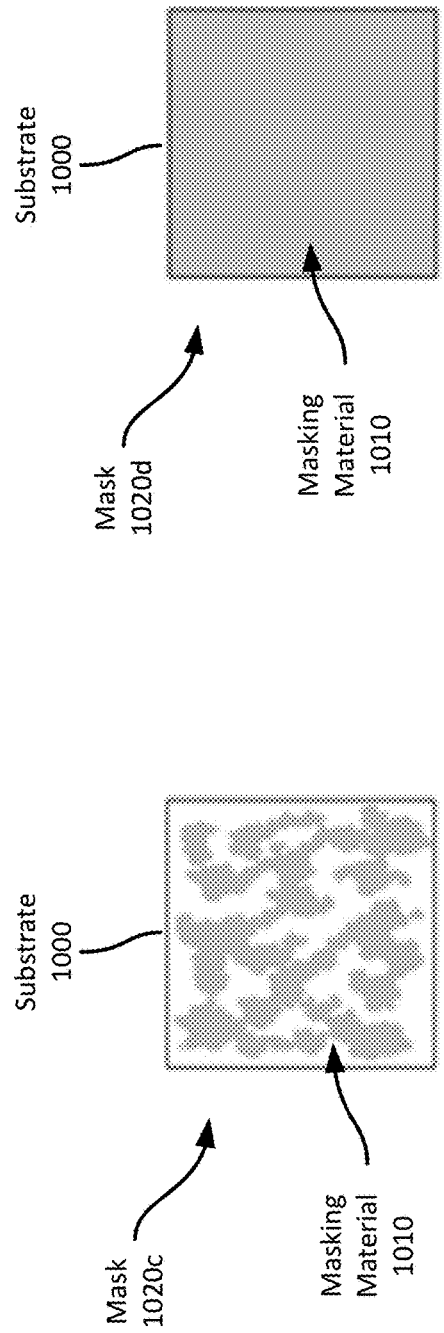

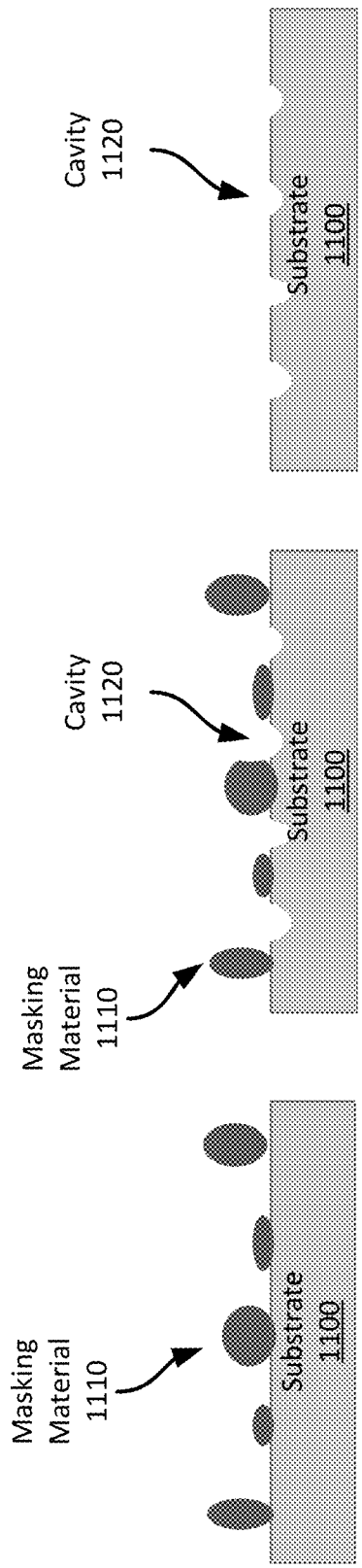

| White Light Interferometer | | Post LCP Etch Best Case | | Enhancement Factor | | Comment |
|---|---|---|---|---|---|---|
| | | Sa (nm) | Sq (nm) | Sa | Sq | |
| Aluminum mask kept | 5 nm | 267 | 348 | 1.37 | 1.41 | Roughness is enhanced |
| | 10 nm | 238 | 316 | 1.22 | 1.28 | Roughness is enhanced |
| | 15 nm | 349 | 334 | 1.78 | 1.35 | Roughness is enhanced by 78% |
| | 20 nm | 261 | 345 | 1.33 | 1.40 | Roughness is enhanced |
| Aluminum mask removed | 5 nm | 243 | 317 | 1.24 | 1.28 | Roughness is enhanced |
| | 15 nm | 258 | 345 | 1.32 | 1.40 | Roughness is enhanced |
| | 20 nm | 295 | 399 | 1.51 | 1.62 | Roughness is enhanced by 62% |
| Bare LCP (control) | NA | 195.6±8.0 | 246.8±15.0 | 1.00 | 1.00 | Baseline control used to calculate enhancement factor |

*FIG. 13*

PACKAGING TECHNIQUES FOR ELECTRONIC DEVICES

CROSS-REFERENCE TO RELATED APPLICATIONS

This application claims priority to U.S. Provisional Patent Application No. 62/663,888 filed Apr. 27, 2018, titled "Packaging Techniques for Electronic Devices," the entirety of which is hereby incorporated by reference.

FIELD

The present application generally relates to packaging techniques, and more specifically relates to packaging techniques for electronic devices.

BACKGROUND

Biosensors may be used over an extended period of time, e.g., days, weeks, or months, and may be used to obtain physiological information about the wearer. For example, invasive biosensors may be used to obtain analyte information from interstitial fluid. Non-invasive biosensors may be used to obtain information relating to cardiac activity or blood flow. Similarly, biostimulators may be used to apply stimuli to a wearer and may be implanted within the wearer. Such biosensors and biostimulators may include sensitive electronics that may be damaged or destroyed if contaminants, such as bodily fluid, enter the device's housing and come into contact with the electronics.

SUMMARY

Various examples are described for packaging techniques for electronic devices. One disclosed method includes defining an electrical trace on a first substrate; physically coupling an electronic component to the first substrate, wherein a portion of the electrical trace completely encircles the electronic component; overlaying a second substrate onto the first substrate, the overlaying causing the second substrate to completely cover the portion of the electrical trace and the electronic component; electrically coupling an electrical power source to the electrical trace to generate a current in the electrical trace; melting the second substrate using heat generated by the current through the electrical trace; and fusing the second substrate to the first substrate to generate a hermetic seal around the electronic component.

Another disclosed method includes defining an electrical trace on a first substrate; creating a plurality of electronic devices on the first substrate, each electronic device comprising an electronic component, each electronic device created on a separate portion of the first substrate, wherein the electrical trace defines boundaries between each electronic device; electrically coupling an electrical power source to the electrical trace to generate a current in the electrical trace; and melting the first substrate using heat generated by the current through the electrical trace to singulate each electronic device of the plurality of electronic devices.

A further disclosed method includes forming a self-assembled mask on a substrate, the self-assembled mask comprising a mask substance and defining a plurality of gaps; applying a first etching substance to the substrate to etch the substrate at locations corresponding to the plurality of gaps, the first etching substance configured to etch the substrate and to not react with the mask substance; and applying a second etching substance to the self-assembled mask to remove the self-assembled mask from the substrate, the second etching substance configured to etch the self-assembled mask but to not react with the substrate.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIGS. 8A-8B show an example substrate having multiple fluid cavities according to this disclosure;

FIGS. 10A-10D show example self-assembling masks according to this disclosure;

FIGS. 11A-11C show example self-assembling masks and surface-roughened substrates according to this disclosure;

FIG. 13 shows a table having experimental results using an aluminum masking material deposited on a substrate;

DETAILED DESCRIPTION

Figure 1:
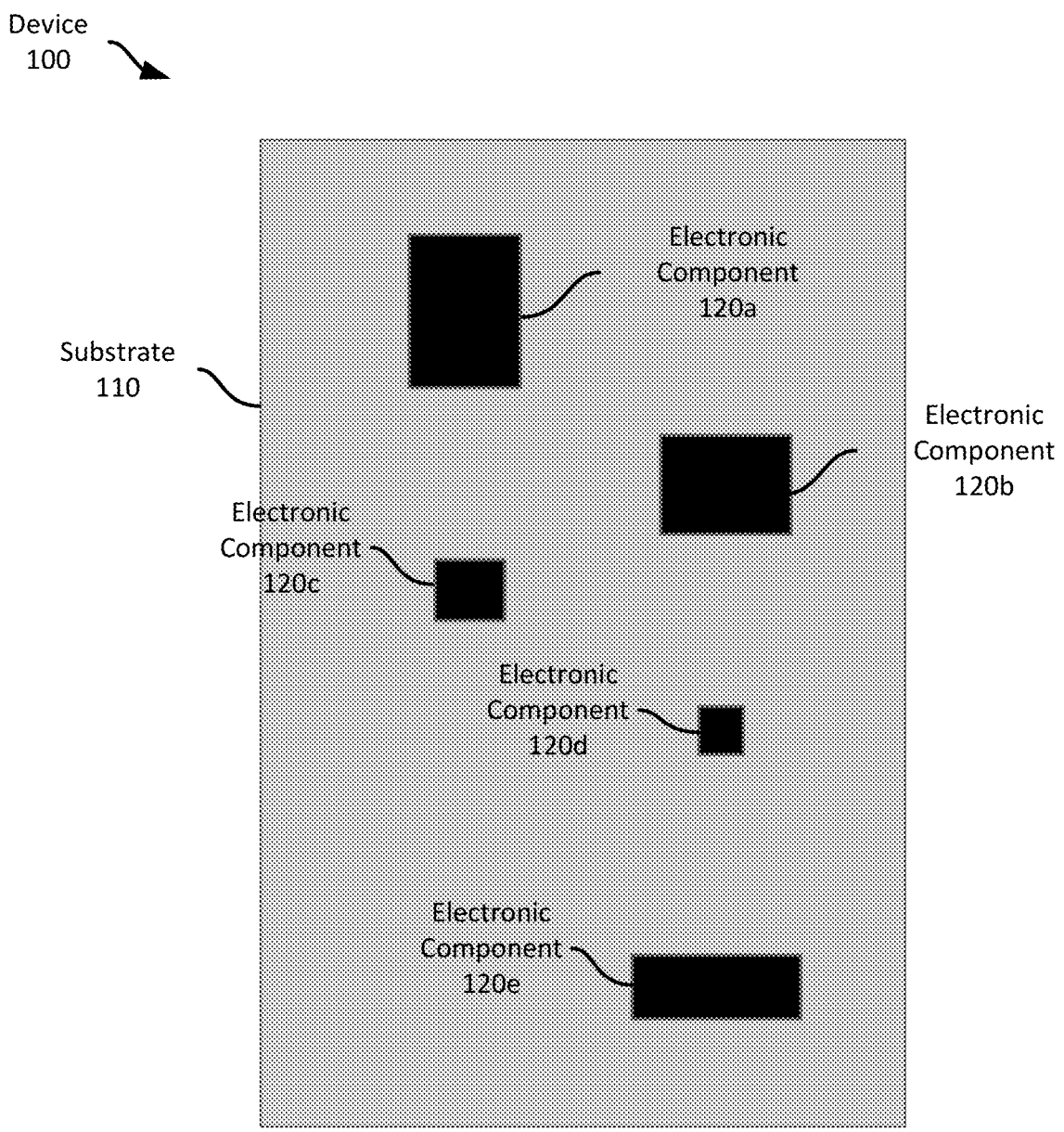
FIG. 1 shows example electronic devices according to this disclosure.

Examples are described herein in the context of packaging techniques for electronic devices. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Electronic devices, including biosensors and biostimulators to be worn or implanted within a wearer, may be susceptible to damage if fluids or other contaminants are able to penetrate the device and come into contact with its electronics. This may be generally true for any electronic device, though some environments, such as within the human body, may present significant risk for such contamination and damage. Thus, it can be desirable to hermetically seal electronics within a package to reduce the chances of contaminants reaching the electronics, or at least to slow their progress.

In one illustrative example according for packaging techniques for electronic devices, an electronics device may be constructed on a substrate, such as a printed circuit board ("PCB") material, e.g., a polyimide or FR-4 material. In addition to electronic components affixed to or deposited on the PCB, an electrical trace may be deposited on the PCB and routed to entirely surround, or encircle, the electronic components within the electrical trace. For example, the electrical trace may be routed around the PCB just inside of its perimeter edge. The electrical trace may be connected to two electrical contacts, each contacting one end of the electrical trace. Such an arrangement may create a resistive heating element, also referred to as a microheater, so that when a voltage is applied across the two contacts, electrical current runs through the electrical trace, heating it.

After the electronic components and electrical trace have been affixed to the PCB, a layer of a liquid crystal polymer ("LCP") substrate is overlaid on the electronics and electrical trace, completely covering them. In this example, pressure is applied to the LCP substrate to hold it in place, though pressure is not required. A power source is then connected to the two electrical contacts and current is flowed through the electrical trace, as described above. The electrical trace outputs heat, which is absorbed by the PCB and the LCP substrate. Sufficient heat is output to melt the LCP substrate into contact with the PCB. After the LCP has melted sufficiently, the power source is disconnected from the electrical contacts and the LCP solidifies and fuses with the PCB, creating a hermetic seal around the electronic components.

Such a technique may allow the use of an LCP substrate, which has a relatively high melting point, e.g., greater than 250 degrees Celsius, but provides high quality hermetic seals, in contexts where applying such high temperatures to the entire PCB and electronic components may damage or destroy them. For example, simply overlaying the LCP substrate on the PCB and heating the entire structure to the LCP substrate's melting point would melt the LCP substrate, but would also subject the PCB and electronic components to the same high temperatures. Instead, the use of the electrical trace as a microheater provides precise heating only where the heat is needed to melt and fuse the LCP substrate to the PCB, away from otherwise sensitive electronic devices. Further, such a technique directly melts the LCP substrate to create the hermetic seal, rather than melting another bonding agent, such as a solder or epoxy, to seal the substrate layers together. Use of such an intermediate bonding agent may couple the LCP substrate to the PCB, but may not provide a strong, hermetic seal around the entirety of the electronics device. Thus, the illustrative example provides a high-quality hermetic seal by directly heating and melting the LCP substrate cover to the PCB substrate.

In addition to creating a hermetic seal, microheaters may be used to singulate individual electronic devices formed on a common substrate, such as a PCB material. For example, multiple electronic devices, e.g., multiple biosensors or biostimulators, may be constructed on a common sheet of substrate. An electrical trace (or multiple electrical traces) may then be formed along the desired perimeters of each biosensor or biostimulator and connected to two electrical contacts, as discussed above. A power source may then be coupled to the electrical contacts to flow current through the electrical trace, thereby heating and cutting the sheet of substrate and singulating the individual electronic devices from each other. Such a technique may also be combined with the hermetic sealing technique discussed above, such as by using one electrical trace to seal the electronics, and a second electrical trace to singulate the devices.

Using electrical traces as microheaters may provide manufacturing advantages over other singulation techniques, such as mechanically cutting, e.g., sawing, the substrate or by using a laser to cut the substrate. Such techniques may be expensive or create significant amounts of debris, which is a potential contaminant.

In addition, in some examples, LCP substrate materials, such as discussed above, may have one or more thin films applied to them during manufacturing, such as to provide biocompatibility or an adhesive to mount a biosensor to a wearer's skin. Further, thin films could be metal traces or contacts used for electrical routing and connection of electronic components, electrodes, etc. In some examples, thin films could include non-metals to create fluidic channels, smooth topographies, or another protective layer.

However, because LCP substrates can be very smooth, obtaining a robust bond with a thin film may be difficult. Thus, in this illustrative example, before the LCP substrate is overlaid on the electronic device to create a hermetic seal, it is processed to roughen the surface to provide enhanced bonding or adhesion characteristics. In this example, a self-assembled mask is grown on a sheet of LCP substrate to the point where the mask partially, but does not completely, forms a film on the surface of the LCP substrate. The partially-masked LCP substrate is then etched using a wet or dry chemical etch to create cavities in locations not covered by the mask. The mask is then removed, leaving the LCP substrate with a partially etched, rough surface that may be suitable to bond thin films to it.

Such a technique may be advantageous over other techniques, such as a maskless wet etching process or heat-emboss molding. Such a maskless etch technique may provide only limited roughening of the LCP substrate, which may be of little to no benefit in applying a thin film. Further, the heat-emboss molding involves heating the LCP substrate until it softens, and then imprinting it with one or more molds with roughening features on them. As discussed above, applying significant heat to the LCP substrate may damage electronics in the underlying device, or it may only allow limited roughness characteristics based on the selected mold(s).

Thus, techniques according to this disclosure may provide packaging techniques to seal and singulate electronic devices, as well as apply thin film layers within or onto the sealed devices. This illustrative example is given to introduce the reader to the general subject matter discussed herein and the disclosure is not limited to this example. The following sections describe various additional non-limiting examples of packaging techniques for electronic devices.

Referring now to FIG. 1, FIG. 1 shows an example electronic device 100. In this example, the electronic device 100 is formed on a substrate 110, such as a PCB material, which has multiple electronic components 120a-e physically coupled to it. And while the substrate 110 is PCB in this example, any suitable substrate material may be employed, including LCP material, soft organic films, plastics, polymers (e.g., polyether ether ketone ("PEEK")), low-melting-point glass sheets or metal foils, etc. The electronic components 120a-e may include any suitable electronics components, including electronic chips, e.g., microprocessors, microcontrollers, application-specific integrated circuits ("ASICs"), etc.; transistors; resistors; capacitors; inductors; diodes; etc. Further, while the example device 100 includes five electronic components 120a-e, any suitable number of electronic components may be employed.

Such an electronic device 100 may be used for any suitable purpose, including in a biosensor or biostimulator. Biosensors include devices that include one or more sensors to sense physiological information about a wearer, such as pulse rate, blood pressure, SpO2 or SvO2, glucose level, lactate level, etc., including drawing blood samples, etc. Biostimulators include devices that can provide physiological stimulus to the wearer, such as by applying voltage or current to nerves or organs, inject materials into the wearer's body, etc.

A biosensor or biostimulator device may be wearable, invasive, or implantable. A wearable device may be an electronic device that can be worn on a wearer's body, such as a watch, a contact lens, a chest strap, an arm band, a wristband, eyeglasses, an earring, etc. Such devices may be worn against the surface of the wearer's skin, or may include one or more invasive components. An invasive device includes components that are inserted beneath the wearer's skin, but where a portion of the device remains outside of the wearer's skin. For example, a continuous glucose monitor ("CGM") may include a sensor wire that is inserted into the wearer's skin to contact the interstitial fluid beneath the surface of the skin, while also including a component that is affixed to the wearer's skin, such as by an adhesive. Implantable devices include devices that are entirely implanted beneath a wearer's skin, within an internal cavity, or attached to an organ of the wearer's body, such as the brain or one or more nerve bundles. It should be appreciated that an implanted device may be connected to another device that has not been implanted, such as via a wired or wireless communication connection.

Further, it should be appreciated that this disclosure is not limited to biosensors or biostimulators. Rather, the techniques described herein may be used in any suitable context that includes packaging electronic devices. Such electronic devices may include any kinds of electronic components, including those discussed above. Further, electronic device may also include mechanical components, such as motors, piezoelectric elements, etc.; optical components, such as lenses, optical filters, etc; etc. Thus, electronic devices broadly include any system that includes such components. Thus, while examples discussed herein may include example biosensors or biostimulators, other types of electronic devices fall within the scope of the present disclosure.

Figure 2A:
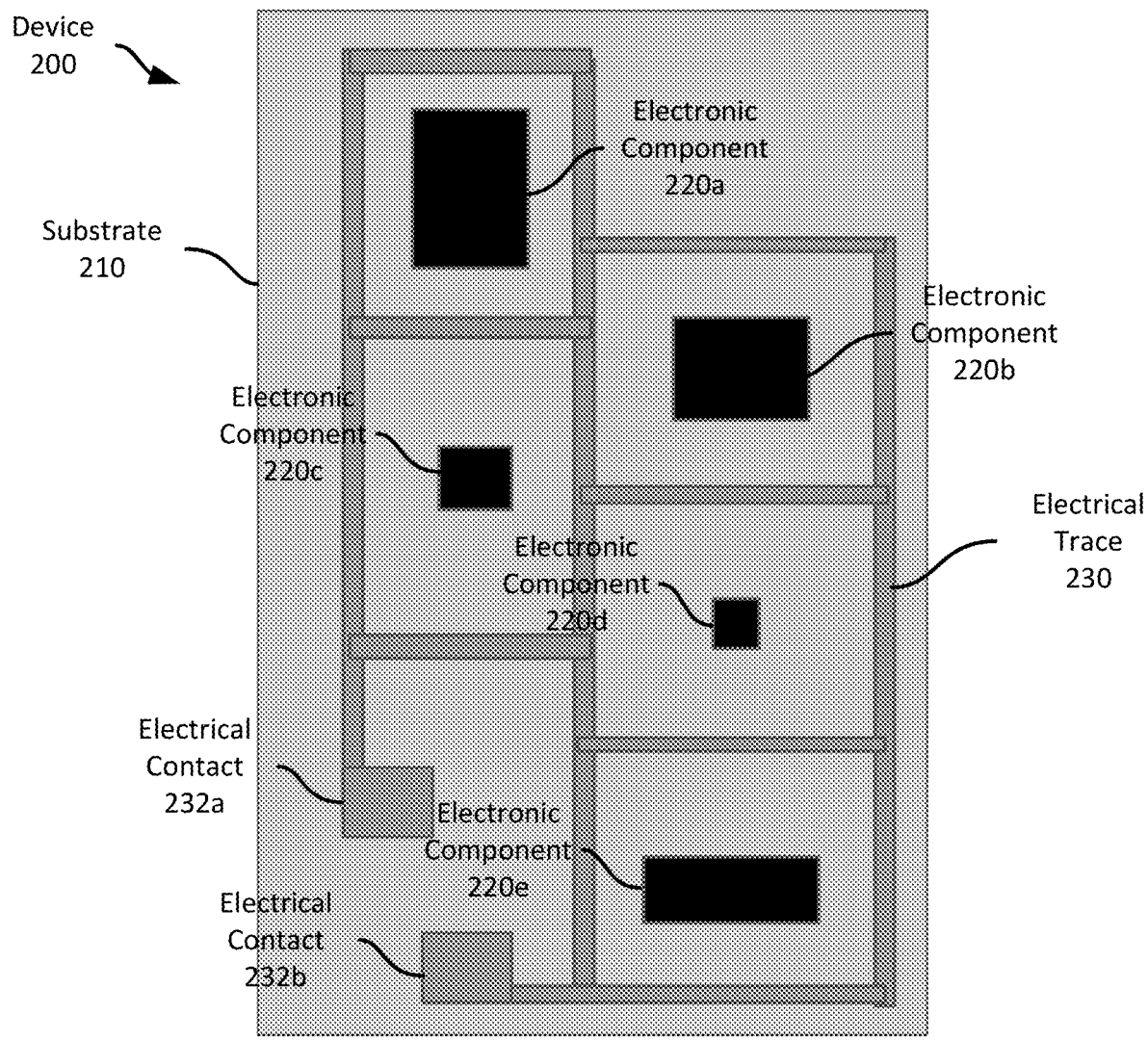
FIGS. 2A-2B show example electronic devices according to this disclosure.

Referring now to FIG. 2A, FIG. 2A shows an example electronic device 200 formed on a substrate 210, such as a PCB material. The electronic device 200 includes multiple electronic components 220a-e, generally as described above with respect to FIG. 1. In addition, an electrical trace 230 has been formed on the substrate 210 and entirely encircles each of the electronic components 230a-c. An electronic component 230a-e is encircled if there are no gaps in the electrical trace 230 running the perimeter of the electronic component.

In this example, each of the electronic components 230a-e is individually encircled; however, the electrical trace 230, in some examples, may collectively encircle all of the electronic components 230a-e without individually encircling each. In some examples, some of the electronic components 230a-e may be individually encircled, while others may be collectively encircled. Further, in some examples, one or more electronic components 230a-e may be individual encircled, and it may further be collectively encircled along with one or more other electronic components 230a-e.

In addition, the electrical trace 230 is electrically coupled to two electrical contacts 232a-b. The electrical contacts 232a-b may be used to connect the electrical trace 230 to a power supply. When connected to a power supply, the power supply may supply a voltage across the electrical contacts 232a-b thereby generating a current in the electrical trace 230. The electrical resistance of the electrical trace 330 to the current generates heat, which may be used to melt and fuse a piece of another substrate material to substrate 210 to seal the electronic components 230a-e.

Figure 2B:
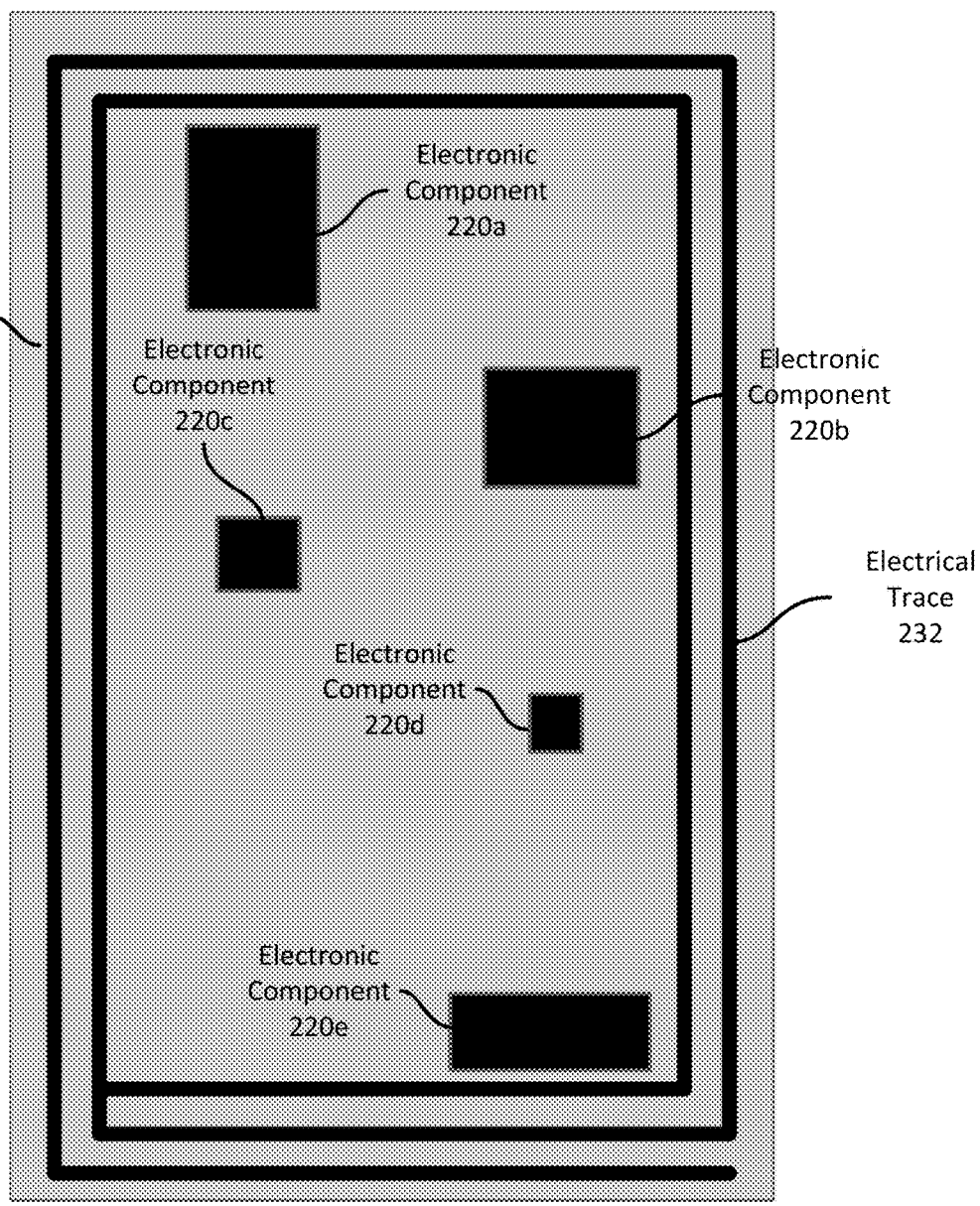

Further, in some examples, the electrical trace 230 may be formed as a coil encircling the electronic components 230a-e, such as may be seen in FIG. 2B. In this example, the electrical trace 232 is formed in a coil to provide wireless inductive coupling with a power source. Thus, separate electrical contacts, such as shown in FIG. 2A, may be omitted, and the electrical coupling with the power source may be wireless.

Figure 3:
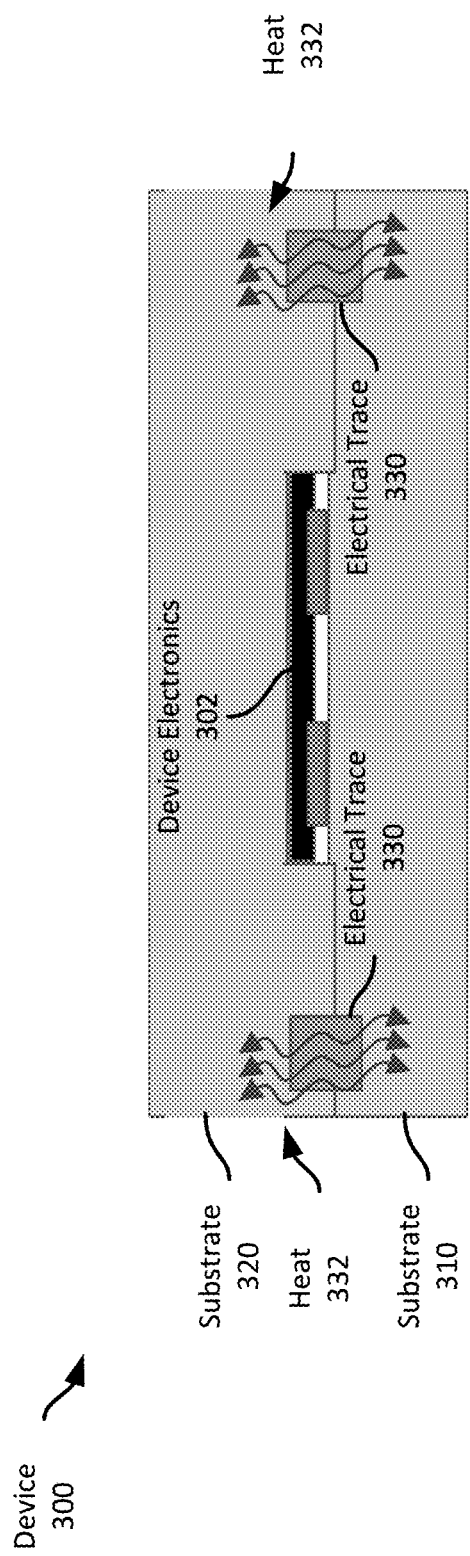
FIG. 3 shows a cross-section of an example electronic device according to this disclosure.

Referring now to FIG. 3, FIG. 3 shows a cross-section of an example electronic device 300 according to this disclosure. The electronic device 300 includes device electronics 302 that have been physically coupled to a substrate 310, such as PCB material. An electrical trace 330 has been formed on the substrate 310 and encircles the device electronics 302, generally as described above with respect to FIGS. 2A-2B.

In this example, a second substrate 320 has been overlaid on top of the device electronics 302, the electrical trace 330, and substrate 310. In this example, the second substrate 320 includes a sheet of LCP material; however, any suitable substrate material may be employed according to different examples, such as soft organic films, plastics, low-melting-point glass sheets or metal foils, etc. After the second substrate 320 has been overlaid, a power source is electrically connected to the electrical trace 330 to generate a current in the electrical trace 330. The current generates heat 332 based on the electrical resistance of the electrical trace 330, which is transmitted to both substrates 310, 320. In this example, the power source provides sufficient current to heat and melt the second substrate 320, but not the first substrate 310. Thus, the heat output by the electrical trace 330 melts the second substrate 320. In some examples, external pressure may be applied to part or all of the second substrate 320 to press the second substrate 320 against substrate 310 and the electrical trace 330 to assist with the sealing process; though in some examples, no external pressure is applied.

After the second substrate 320 has melted along the length of the electrical trace 330 encircling the device electronics 302, the power source is disconnected and the melted substrate is allowed to cool and solidify, thereby bonding to substrate 310 and sealing the device electronics 302 between the second substrate 320 and substrate 310. In this example, the sealing process creates a hermetic seal around the device electronics 302. As discussed above, the seal is created by melting the second substrate. No additional bonding agent, such as an epoxy or solder, is employed to create seal between substrate 310 and the second substrate 320. Thus, by melting the substrate without the use of another bonding agent, a hermetic seal is created between the substrate 310 and the second substrate 320.

While in this example, the electrical trace was formed on substrate 310, in some examples, in may be formed on substrate 320 instead. Thus, the electrical trace 330, or portions of the electrical trace 330, may be formed on a separate substrate than the device electronics 302. Further, as discussed above with respect to FIG. 2B, the electrical trace 330 may be formed as a coil encircling the device electronics 302. Thus, separate electrical contacts may be omitted, and the electrical coupling with the power source may be wireless.

Figure 4A:
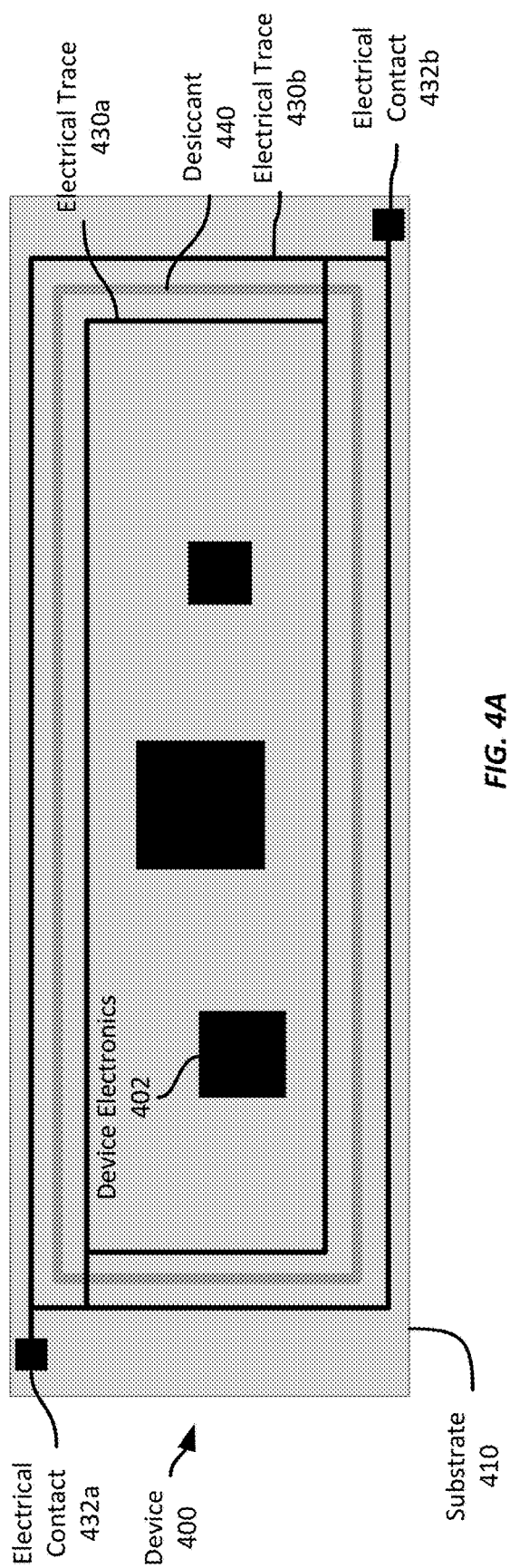
FIGS. 4A-4B show an example electronic device according to this disclosure.
Figure 4B:
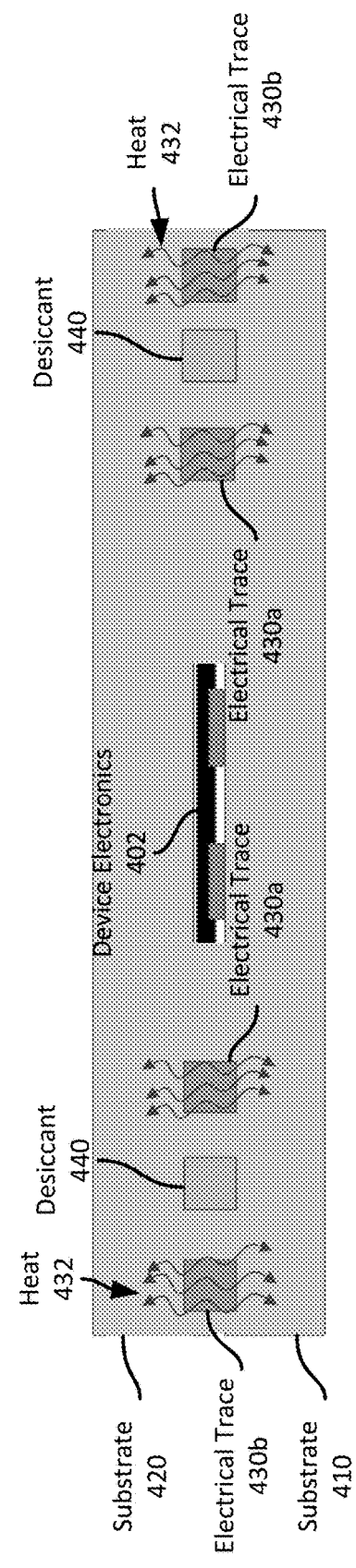

Referring now to FIGS. 4A-4B, FIG. 4A shows a top-down view of an electronic device 400 according to this disclosure, while FIG. 4B shows a cross-section of the example electronic device 400. The electronic device 400 of FIGS. 4A-4B generally includes the same components as the electronic device 300 described above with respect to FIG. 3. It includes device electronics 402 affixed to a substrate 410. An electrical trace 430a-b is formed on the substrate 410 and encircles the device electronics and is electrically coupled to two electrical contacts (not shown). In addition, a desiccant 440 is also disposed on the substrate 440 and encircles the device electronics 402. In this example, the desiccant 440 encircles the device electronics 402 outside of, but concentrically with, a first portion 430a of the electrical trace 430a-b, and inside of a second portion 430b of the electrical trace 430a-b. In this example, the electrical trace 430a-b is a single contiguous electrical trace; however, in some examples, the first portion 430a of the electrical trace 430a-b may be separate from the second portion 430b of the electrical trace 430b. In one such example, each separate electrical trace may be electrically coupled to a separate pair of electrical contacts; however, in some examples, some or all of the separate electrical traces may share the same pair of electrical contacts.

Similar to the example shown in FIG. 3, a second substrate 420 is overlaid on top of the device electronics 402, the electrical trace 430a-b, and the desiccant 440. In this example, the second substrate 420 is an LCP substrate; however, any suitable substrate material may be employed according to different examples. After the second substrate 420 has been positioned, a power source is electrically coupled to the electrical trace 430a-b and transmits a current through the electrical trace 430a-b. The current generates heat 432 via the electrical trace's electrical resistance generally as described above, which melts the second substrate 420. After the second substrate 420 has been sufficiently melted, the power source is disconnected, which allows the second substrate 420 to cool and bond to substrate 410 creating a seal between the two substrates 410, 420. In this example, because the device electronics 402 are encircled by the electrical trace 430a-b, a hermetic seal is created. Further, the desiccant 440 is also hermetically sealed between the two substrates 410, 420, and can provide further resistance to encroachment of contaminants if the heat-seal were to be compromised. As discussed above, no additional bonding agent, such as an epoxy or solder, is employed to create seal between substrate 410 and the second substrate 420. Thus, by melting the substrate without the use of another bonding agent, a hermetic seal is created between the substrate 410 and the second substrate 420.

Further, while in this example, the electrical trace 430a-b was formed on substrate 410, in some examples, in may be formed on substrate 420 instead. Thus, the electrical trace 430a-b, or portions of the electrical trace 430a-b, may be formed on a separate substrate than the device electronics 402. Further, as discussed above with respect to FIG. 2B, the electrical trace 430a-b may be formed as a coil encircling the device electronics 402. Thus, separate electrical contacts may be omitted, and the electrical coupling with the power source may be wireless.

Figure 5:
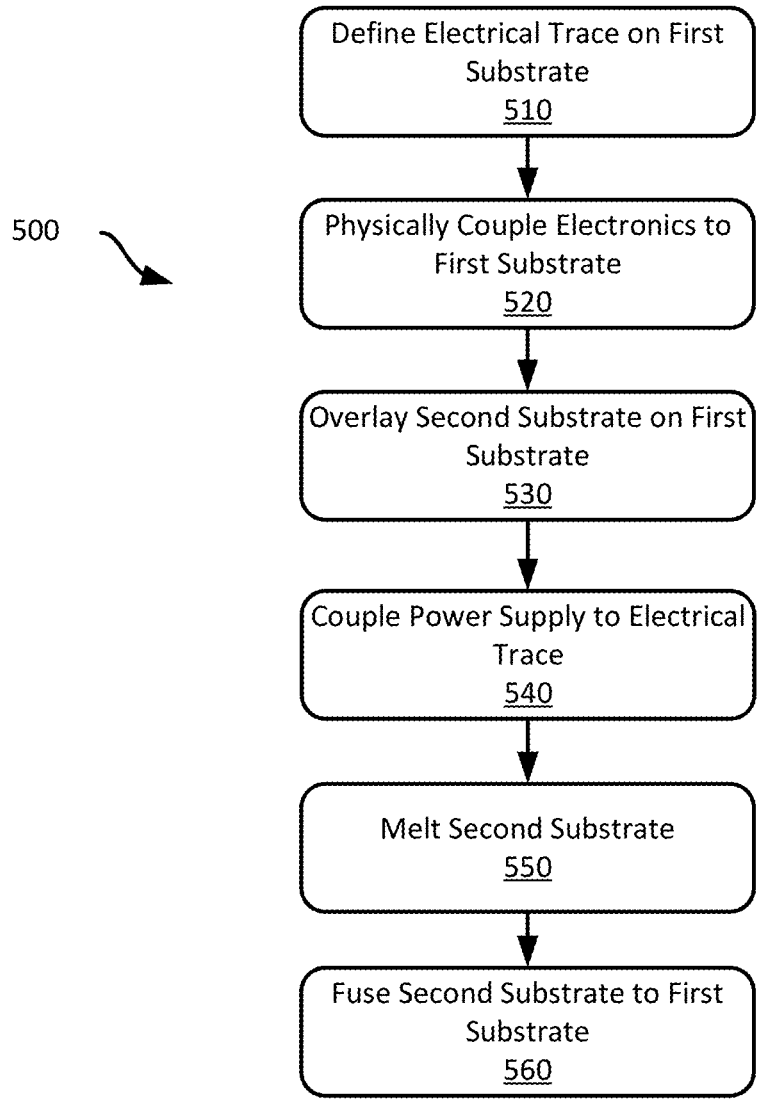
FIG. 5 shows an example method according to this disclosure.

Referring now to FIG. 5, FIG. 5 shows an example method 500 according to this disclosure. The description of FIG. 5 will be made with respect to the example device 300 shown in FIG. 3, though any suitable device or arrangement may be employed.

At block 510, an electrical trace 330 is defined on a first substrate 310. Any suitable conductive material may be employed, such as copper, aluminum, etc., to define the electrical trace 330. The electrical trace 330 is formed to encircle locations where one or more electrical components will be positioned on the first substrate 310. In some examples, the electrical trace 330 will individually encircle one or more electronic components, while in some examples, the electrical trace 330 will collectively encircle some or all of the electronic components, or both individually encircle one or more electronic components and collectively encircle some or all of the electronic components. In this example, the electrical trace is electrically coupled to two electrical contacts formed on the first substrate 310. The electrical contacts may be formed at block 510 or at any suitable time during the manufacturing process, such as at block 530. Further, while in this example, the electrical trace 330 is formed on the first substrate, in some examples, it may be formed on the second substrate 320 instead. Thus, electronic components 302 may be physically coupled to the first substrate 310, while the electrical trace 330 may be applied to the second substrate. 320

At block 520, one or more electronic components, illustrated as the device electronics 302, are physically coupled to the first substrate 310. Any suitable electronic components may be employed according to different examples and device designs. It should be appreciated that while block 520 follows block 510 in this example, block 520 may precede block 510 in some examples, or they may be performed at substantially the same time.

At block 530, a second substrate 320 is overlaid on the first substrate 310 and on top of the device electronics 302 and the electrical trace 330. In this example, the second substrate is an LCP substrate and is overlaid to completely cover the device electronics 302 and the electrical trace 330; however, in some examples, the second substrate 330 may only cover a portion of the device electronics 302. For example, a portion of the device electronics 302 may be designed to operate in an environment having various contaminants, e.g., a sensor. In one such example, such portion of the device electronics 302 may not be covered by the second substrate 320.

At block 540, a power supply is coupled to the electrical trace 330. In this example, the power source is electrically coupled to the electrical contacts to supply a voltage across the contacts and to supply a current to the electrical trace 330. In some examples, however, the power source may be coupled to any two points on the electrical trace 330 so long as current traverses the entire electrical trace encircling the device electronics 302.

At block 550, the current supplied by the power source causes the electrical trace 330 to generate heat, which melts the second substrate 320 at locations corresponding to the electrical trace 330. In this example, the heat generated by the electrical trace 330 is sufficient to melt the second substrate 320, but not the first substrate 310. Though in some examples the heat may be sufficient to melt both substrates 310, 320.

At block 560, the second substrate 320 is fused to the first substrate 310. In this example, the power source stops supplying current to the electrical trace 330, which allows the electrical trace 330 and the substrates 310-320 to cool, thereby allowing the second substrate 320 to solidify and fuse with the first substrate 310. In examples where both substrates 310, 320 melt, both cool and fuse to each other.

Figure 6:
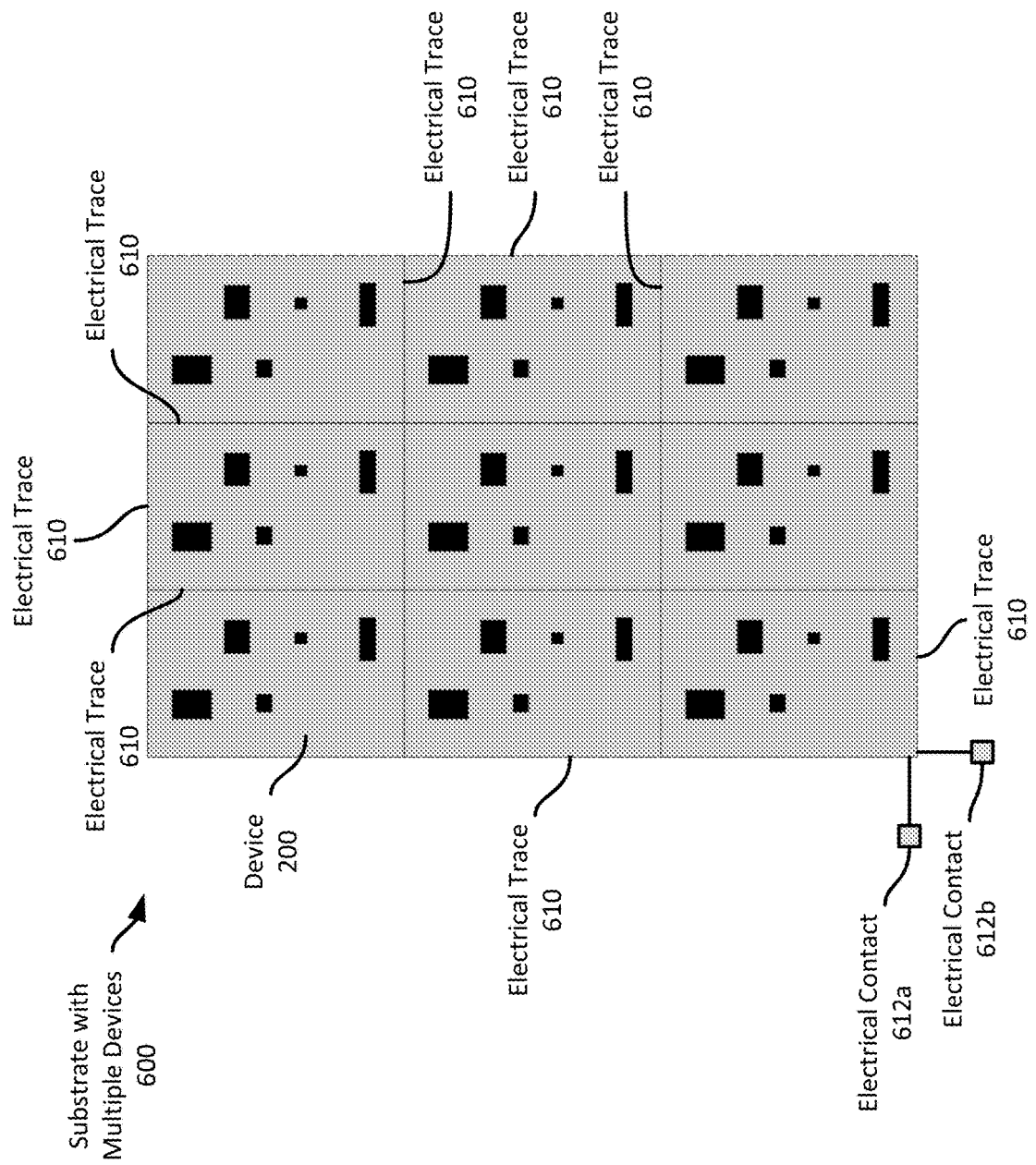
FIG. 6 shows an example substrate having multiple electronic devices according to this disclosure.

Referring now to FIG. 6, FIG. 6 shows an example substrate 600 having multiple electronic devices 300 formed on it. For example, a single PCB may have multiple copies of the same (or different) electronic devices formed on it. The PCB may then be cut to singulate the individual electronic devices. In this example, the electronic devices 300 have been formed in a grid pattern and an electrical trace 610 forming boundaries between the discrete electronic devices 300 has been formed on the substrate 600 as well. The electrical trace 610 is electrically coupled to two electrical contacts 612a-b to enable a power source to electrically couple to the electrical trace 610. In this example, the electrical trace 610 is formed to enable cutting of the substrate 600 to singulate the individual electronic devices 300. Thus, when a power source is electrically coupled to the electrical contacts 612a-b and supplies sufficient electrical current, the electrical trace 610 generates and outputs heat to the substrate 600, melting or otherwise cutting substrate material away to singulate the devices 300.

In some examples, the electronic devices 300 also include one or more electrical traces described above with respect to FIGS. 2A-5 to enable hermetic sealing of the devices 300 with a second substrate material (not shown). Further, such hermetic sealing may occur prior to singulation of the electronic devices 300. For example, the electronic devices 300 may be formed as described above with respect to FIG. 5. Subsequently, a power source may be electrically coupled to the electrical contacts 612a-b to supply current to the electrical trace 610. The heat generated by the electrical trace 610 may cut both the substrate 600 and the second substrate, thereby singulating the device 300.

Figure 7:
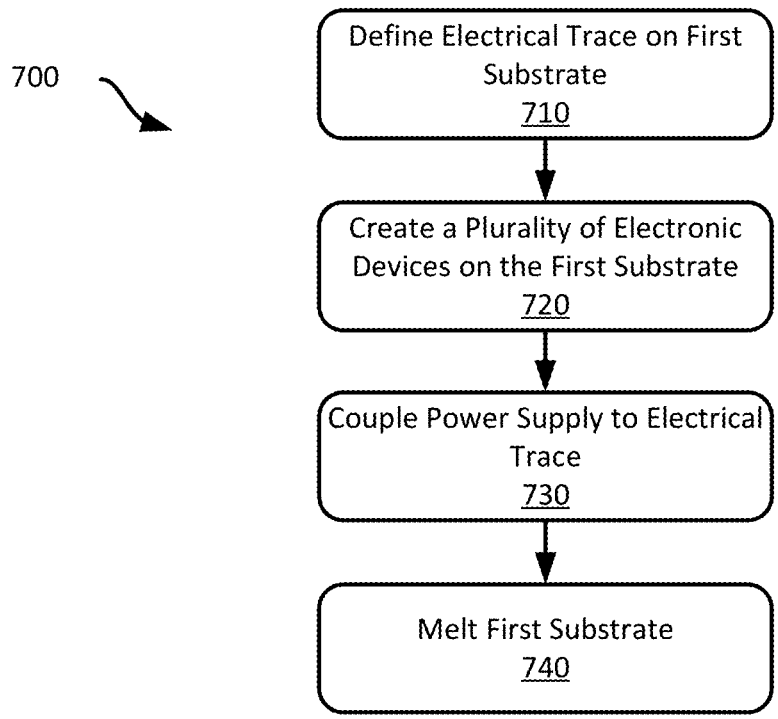
FIG. 7 shows an example method according to this disclosure.

Referring now to FIG. 7, FIG. 7 shows an example method 700 according to this disclosure. The description of FIG. 7 will be made with respect to the example substrate 600 shown in FIG. 6, though any suitable device or arrangement may be employed.

At block 710, an electrical trace 610 is formed on a first substrate 600. In this example, the first substrate is a PCB material; however, any suitable substrate may be employed. In this example, the electrical trace 610 is shaped to define perimeters for a plurality of electronic devices formed, or to be formed, on the first substrate 600. It should be appreciated that while a single contiguous electrical trace 610 is employed in this example, in some examples, multiple electrical traces may be employed to define perimeters for one or more electronic devices formed, or to be formed, on the first substrate 600. In this example, the electrical trace 610 is electrically coupled to two electrical contacts 612a-b formed on the first substrate 600. The electrical contacts 612a-b may be formed at block 710 or at any suitable time during the manufacturing process.

At block 720, a plurality of electronic devices 300 are created on the substrate 600 within the perimeters defined by the electrical trace 610. Each electronic device 300 is formed generally as described above with respect to block 520 of the method of FIG. 5. It should be appreciated that while block 710 precedes block 720 in this example, in some examples, block 720 may be performed before block 710, or they may be performed at substantially the same time.

At block 730, a power supply is coupled to the electrical trace 610. In this example, the power source is electrically coupled to the electrical contacts 612a-b to supply a voltage across the contacts 612a-b and to supply a current to the electrical trace 610. In some examples, however, the power source may be coupled to any two points on the electrical trace so long as current traverses the electrical trace 610. Further, in some examples, the electrical trace may be formed in a coil shape to enable wireless inductive coupling with a power source. In such examples, a physical electrical coupling may not be required, and instead, the power source may be electrically coupled using wireless inductive coupling.

At block 740, heat generated by the current flowing through the electrical trace 610 melts the first substrate 600. In this example, the heat melts the PCB or other suitable substrate material, thereby singulating the electronic devices 300.

It should be appreciated that the method 700 shown in FIG. 7 may be performed in conjunction with other example methods according to this disclosure, such as example methods according to the method 500 of FIG. 5. Such a method may be performed at any time before, during, or after the method 700 of FIG. 7 is performed. For example, the method 500 of FIG. 5 may be performed at block 720.

Referring now to FIGS. 8A-8B, FIG. 8A illustrates an example packaging technique for fluids within fluid cavities. In this example, a suitable substrate 810 has been supplied and formed with multiple fluid cavities 802a, in this example, eight fluid cavities have been formed. On the substrate 810, electrical traces 830 have been defined to encircle each of the fluid cavities and to terminate at two electrical contacts 812a-b, which are also formed on the substrate 810. Subsequently, a fluid 804a has been dispensed in each of the fluid cavities 802a. It should be appreciated that the same fluid or other material need not be dispensed into each cavity 802a. Rather, any combination of suitable fluids or other materials may be dispensed into the cavities as needed.

Referring to FIG. 8B, to seal the fluid 804a within the cavities 802a, a second substrate 820, such as an LCP material, is laid overtop of substrate 810 and the respective cavities 802a. After the second substrate 820 has been positioned, the electrical contacts 812a-b are connected to a power source (not shown), and electrical current flows through the electrical trace 830, it heats and melts the second substrate 820 to the first substrate 810, thereby sealing the fluid within the fluid cavity.

While this example illustrates the use of a fluid stored within the fluid cavity 802a, it should be appreciated that other materials may be stored in such cavities, such as pills or capsules, powders, slurries, etc.

Figure 9:
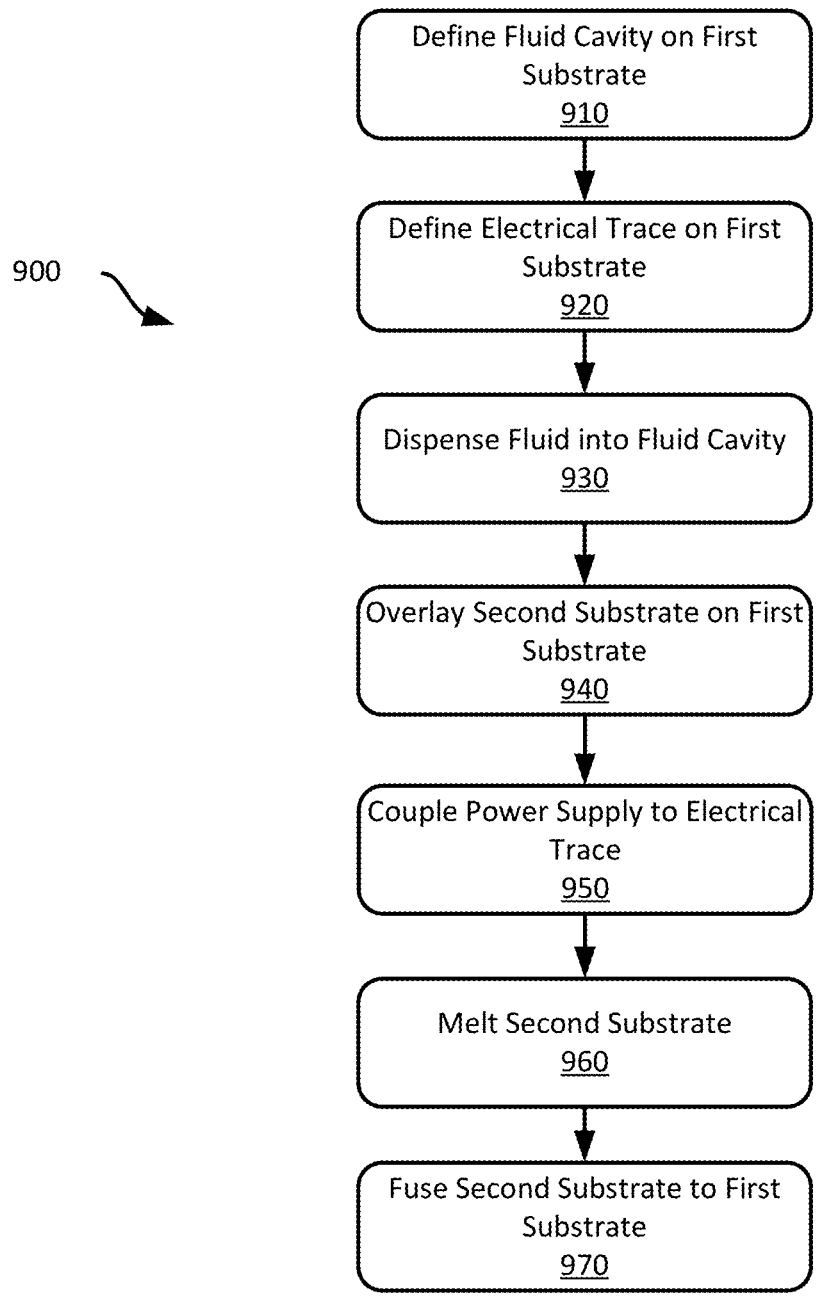
FIG. 9 shows an example method according to this disclosure.

Referring to FIG. 9, FIG. 9 shows an example method 900 according to this disclosure. In this example, the method 900 will be described with respect to the example shown in FIGS. 8A-8B; however it should be appreciated that other examples according to this disclosure may be employed as well.

At block 910, one or more fluid cavities is defined within a first substrate 810. For example, the substrate may be created with defined fluid cavities. Alternatively, the cavities may be formed in the substrate 810 by heating it and using a vacuum or a mold.

In some examples, it should be appreciated that block 910 may simply involve obtaining or otherwise providing a substrate 810 with one or more cavities defined in it.

At block 920, an electrical trace 830 is defined on the first substrate 810 generally as discussed above with respect to block 510 of FIG. 5.

At block 930, a fluid or other substance is placed within one or more of the cavities. For example, an aqueous solution, a pill or capsule, a powder, etc. may be placed in one or more of the cavities.

At block 940, a second substrate 820 is overlaid on the first substrate generally as discussed above with respect to block 530 of FIG. 5.

At block 950, a power supply is coupled to the electrical trace 830 generally as described above with respect to block 540 of FIG. 5.

At block 960, the second substrate 820 is melted generally as described above with respect to block 550 of FIG. 5.

At block 970, the second substrate 820 is fused to the first substrate 810 generally as discussed above with respect to block 560 of FIG. 5.

Referring now to FIGS. 10A-10D, FIGS. 10A-10D show an example packaging technique for biosensors and biostimulators. In this example, a self-assembled mask is formed on a surface of a substrate 1000, such as a second substrate 320, 420 shown in FIGS. 3 and 4. Any suitable substrate material, such as LCP or PEEK (e.g., in a flexible configuration), or rigid substrates, such as glass or quartz, may be employed according to this example. FIGS. 10A-D illustrates different stages of creating self-assembling masks 1020a-d. In this example, a masking material 1010 is deposited, such as by thermal evaporation or sputtering, on the substrate 1000 over time to build up a mask 1020a-d. In some examples, a suitable thickness of the deposited masking material is between substantially 5 and 40 nanometers ("nm"), inclusive. Suitable masking materials include aluminum, copper, gold, chromium, etc.

Over time, as more masking material 1010 is deposited, the mask 1020a initially includes individually dispersed clusters of masking material 1010, followed by joining of clusters to create a mask 1020b having islands of masking material 1010. The islands of masking material may further accumulate additional masking material 1010 and join to create links between different islands of masking material to create a further mask 1020c. Finally, sufficient masking material is deposited to form a continuous film mask 1020d over the entire portion of substrate. According to this disclosure, any of self-assembled masks 1020a-c may be employed, referred to as masks 1020a-c that define a plurality of gaps; however, the continuous film mask 1020d may not be suitable. Though as discussed below with respect to FIGS. 15A-15B, thermal heating to create a discontinuous self-assembled mask may be employed even in scenarios where a continuous film mask is deposited on the substrate.

In this example, after the masking material has been deposited, the substrate with the deposited masking material is heated to help bond the masking material to the substrate. Suitable temperatures and heat times for such a process are based on the metal material that is used, the substrate material, and the activation energy between the substrate and the masking material. In addition, the thickness of the initial masking layer may help adjust the heat-soak times; however, temperatures between approximately 100-350 degrees Celsius with heat-soak times between approximately ten minutes to three hours may be sufficient for most substrate-mask combinations. Further, depending on the substrate, an activation energy may be modified, such as by using a chemical treatment, including oxidizing the substrate (e.g., oxidizing a silicon substrate), nitrogenize the substrate (e.g., nitrogenizing a silicon (Si) substrate to form a thin $Si_3N_4$ layer), reacting the substrate with hexamethyldisilazane ("HMDS"), etc.

Such a heat-soak process can also advantageously cause the deposited masking material to coalesce into discrete particles. This can help provide a randomized discontinuous mask layer on the substrate, even if the initial deposition resulted in a significant portion of the substrate being covered by the masking material. An example of this can be seen in FIGS. 15A-15B.

Figure 15B:
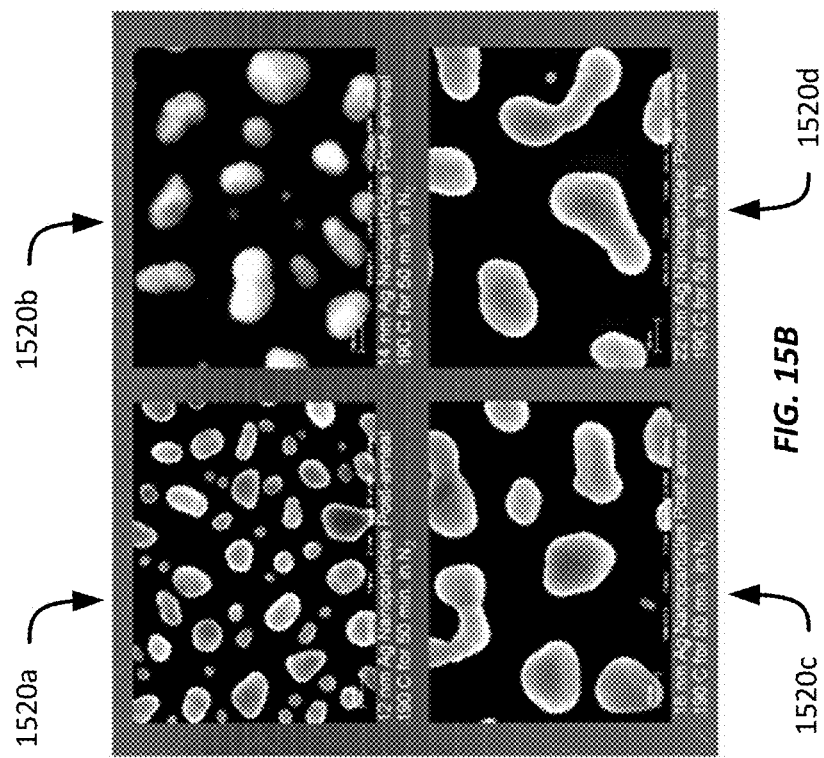
FIG. 15B shows the deposited mask material of FIG. 15A after a heat soak.
Figure 15A:
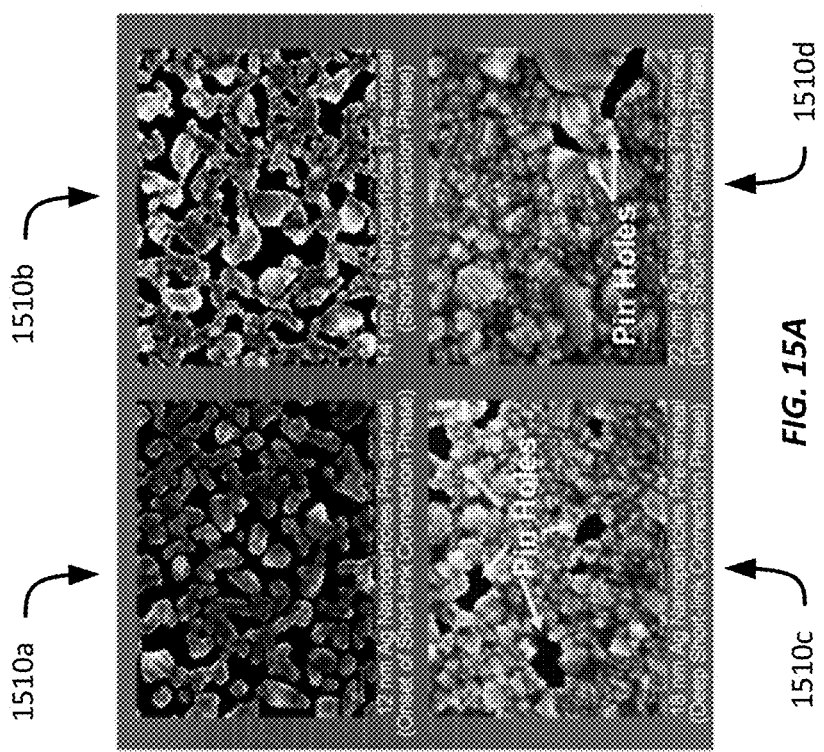
FIG. 15A shows deposited mask material on a substrate after different deposition times.

FIG. 15A illustrates deposited mask material on a substrate after different deposition times 1510a-d. As can be seen, in image 1510a, nanoparticles of a silver mask material have a size of approximately 12 nm with substantial gaps visible between the particles. The particle sizes grow until adjacent particles join together, until ultimately only a few small gaps are visible in image 1510d.

FIG. 15B illustrates the same mask layers shown in FIG. 15A; however, the mask layers in FIG. 15B have been heat-soaked at 190 degrees Celsius for 50 minutes. As can be seen, the particles in each mask layer have coalesced into discrete particles, providing a discontinuous mask layer on the underlying substrate. Such an effect is visible even in image 1520d, which is the resulting mask layer following a heat-soak of the mask layer shown in image 1510d. Thus, a continuous, or nearly continuous, thin film of mask material may still be rendered into a suitable discontinuous mask layer via a thermal soak process.

Referring now to FIGS. 11A-11C, FIGS. 11A-11C illustrate the use of self-assembling masks to create surface roughness on a substrate. FIG. 11A shows a cross-section of a substrate 1100, such as an LCP substrate material, having a self-assembled mask formed on its surface from a masking material 1110. The self-assembled mask may be any suitable self-assembled mask that defines a plurality of gaps to expose the underlying substrate 1100, such as the masks 1020a-c shown in FIGS. 10A-10C.

FIG. 11B shows the substrate 1100 after an etching material has been applied to the substrate. The etching material in this example is configured to etch the substrate 1100 while not affecting the masking material 1110. Suitable etching materials include wet chemicals, such as acids, or dry plasma using reactive gases. Thus, the etching material forms cavities 1120 in the substrate at locations not covered by the masking material 1110.

Figure 12:
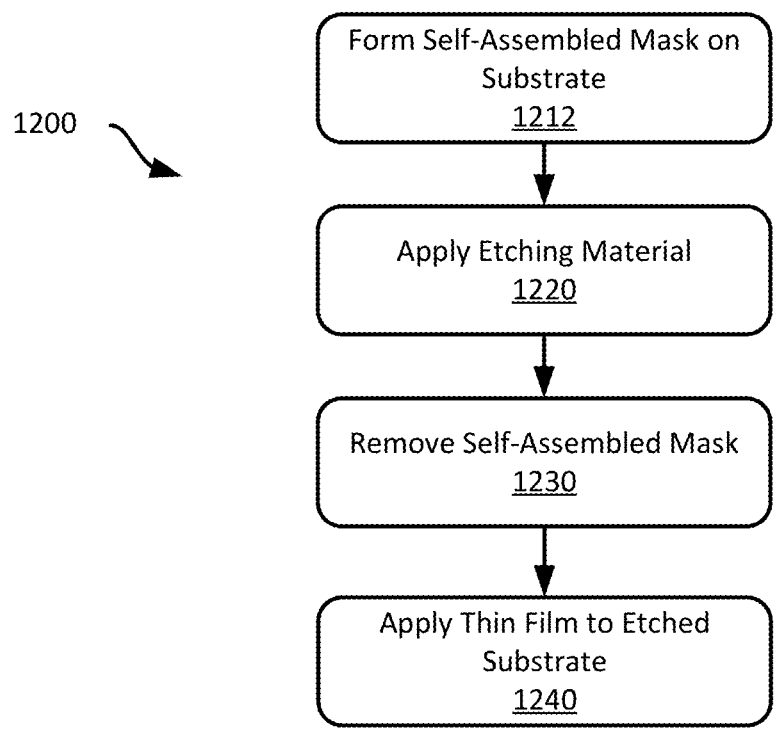
FIG. 12 shows an example method according to this disclosure.

FIG. 11C shows the substrate 1100 after a second etching material has been applied to the substrate 1100 and masking material 1110. The second etching material is configured to etch the masking material 1110 but not the substrate 1100. Thus, at FIG. 11C, the substrate 1100 has been pitted by the etching material, while other portions of the substrate 1100 remain unaffected. The substrate 1100 defining the cavities 1120 may then have a rough surface to enable better bonding or adhesion with other substances, such as one or more thin films. In some examples, thin films could be metal traces or contacts used for electrical routing or connection of electronic components, electrodes, etc. In some examples, thin films could include non-metals to create fluidic channels, smooth topographies, or another protective layer Referring now to FIG. 12, FIG. 12 shows an example method 1200 according to this disclosure. The method 1200 will be described with respect to FIGS. 10 and 11, though any suitable examples according to this disclosure may be employed.

At block 1210, a self-assembled mask 1020a-c defining a plurality of gaps is formed on a substrate material 1000. In this example, the self-assembled mask 1020a-c is formed by thermal evaporation of a suitable masking material 1010, such as aluminum, copper, chromium, gold, etc. Any suitable self-assembled mask 1020a-c may be employed; however, a continuous film mask 1020d covering the entire substrate may be unsuitable. Further, while evaporation of the masking material 1010 is employed in this example, in some examples, sputtering of the material may be employed instead. In this example, masking material 1010 is applied to the substrate 1000 to create a mask having a thickness of between substantially 5 nm to 40 nm, inclusive. Though any suitable thickness may be employed At block 1220, a first etching material is applied to the substrate 1000, 1100 and self-assembled mask 1020. In this example, the first etching material is configured to form one or more cavities 1120 in the substrate 1000, 1100, such as may be seen in FIG. 11B. In this example, the first etching material is a dry-plasma etch. However, it should be appreciated that suitable chemicals may be employed to perform a wet chemical etch in the substrate 1000.

At block 1230, after one or more cavities have been formed in the substrate 1000, 1100, the self-assembled mask is removed by using a second etching material configured to etch the masking material 1010, 1110, but not the substrate 1000, 1100. Suitable second etching materials include wet chemicals, such as acids. For example, if the masking material is aluminum, the second etching material may include phosphoric acid. It should be appreciated that block 1230 may be omitted in some examples.

For example, referring to FIG. 13, FIG. 13 shows a table having experimental results using an aluminum masking material deposited on a substrate. As is shown, the test results indicate whether the aluminum mask layer was kept or removed, and further indicate the thickness of the aluminum mask layer for each test. After the aluminum mask was applied and the underlying substrate was etched (using a dry-plasma etch), the surface roughness was quantified using two techniques, Sa and Sq. For several of the tests, the aluminum mask layer was removed before the surface roughness was quantified. In general, the larger the Sa or Sq value, the rougher the surface. Thus, in the case where the aluminum mask was kept, a 15 nm mask layer provided the greatest effect roughness (Sa value of 1.78), while an initial aluminum mask layer of 20 nm provided the greatest effective roughness (Sq value of 1.62) value when the mask layer was removed. Though it should be appreciated that both the Sa and Sq values may be considered together to determine the proper mask height and whether to remove the mask or not. However, surface roughness was increased in each test, and a suitable level of roughness may be obtained even if different mask depths are used or even if the mask layer is removed.

Figure 14:
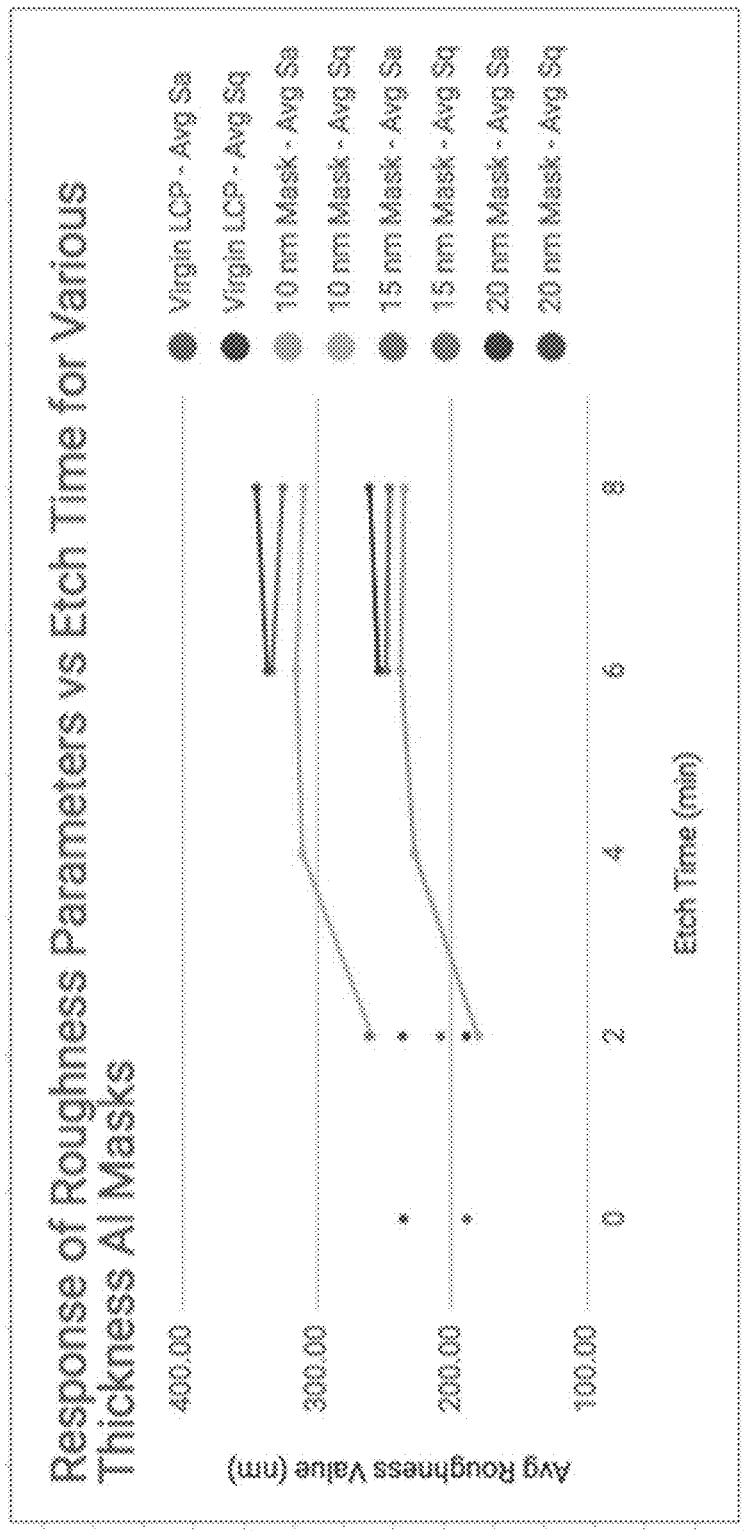
FIG. 14 shows indications of the surface roughness based on etch times for different mask thicknesses.

FIG. 14 provides further indication of the surface roughness based on the etch time for each respective mask thickness (showing both Sa and Sq curves). In particular, as can be seen, by approximately 8 minutes, little to no additional increase in surface roughness was achieved.

Referring again to FIG. 12, at block 1230, in some examples, leaving the masking material may provide other advantages, including increased structural integrity or enhanced material properties. For example, the mask may also provide an adhesion layer for other materials, such as gold or other noble metals.

At block 1240, after the self-assembled mask has been removed, a thin film may be applied to the etched substrate. The formation of the cavities 1120 on the substrate 1110 may roughen the surface of the substrate 1110 to provide a better bonding or adhesion surface for the thin film material.

It should be appreciated that the method 1200 of FIG. 12 may be performed in conjunction with one or more other methods 500, 700 according to this disclosure. For example, the method 1200 of FIG. 12 may be performed at block 720 of the method 700 shown in FIG. 7, or after block 560 of the method 500 shown in FIG. 5; however, any suitable time during such methods may be employed.

Some of the methods described herein may be performed by robotic manufacturing components controlled by software executed by a processor or may be implemented as specifically-configured hardware, such as field-programmable gate array (FPGA) specifically to execute the various methods. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
   defining an electrical trace on a first substrate;
   physically coupling an electronic component to the first substrate, wherein a portion of the electrical trace encircles a portion of the first substrate having the electronic component;
   overlaying a second substrate onto the first substrate, the overlaying causing the second substrate to cover the portion of the electrical trace, the electronic component, and the portion of the first substrate;
   electrically coupling an electrical power source to the electrical trace to generate a current in the electrical trace;
   melting the second substrate using heat generated by the current through the electrical trace; and
   fusing the melted second substrate to the first substrate to generate a hermetic seal around the portion of the first substrate and the electronic component.

2. The method of claim 1, wherein the electrical trace defines a coil and is configured to electrically couple to the electrical power source via wireless inductive coupling.

3. The method of claim 1, wherein the electrical trace is electrically coupled to a first electrical contact and a second electrical contact, and electrically coupling the electrical power source to the first and second electrical contacts.

4. The method of claim 1, wherein the second substrate comprises a liquid crystal polymer.

5. The method of claim 1, further comprising physically coupling an electronic component to the first substrate within the portion of the first substrate.

6. The method of claim 5, wherein physically coupling the electronic component to the portion of the first substrate comprises physically coupling a plurality of electronic components to the portion of the first substrate;
   the electrical trace encircles the plurality of electronic components; and
   fusing the second substrate to the first substrate generates a hermetic seal around the plurality of electronic components.

7. The method of claim 6, wherein the electrical trace individually and encircles at least two electronic components of the plurality of electronic components.

8. The method of claim 1, wherein the portion of the first substrate defines a cavity.

9. The method of claim 8, further comprising disposing a substance within the cavity.

10. The method of claim 8, wherein the first substrate has a plurality of portions, and wherein each portion defines a cavity, and wherein each cavity is encircled by an electrical trace.

11. A device comprising:
    a first substrate;
    an electronic component coupled to the first substrate;
    an electrical trace disposed on the first substrate, a portion of the electrical trace encircling a portion of the first substrate having the electronic component; and
    a second substrate positioned over the portion of the first substrate, the electronic component, and the portion of the electrical trace, the second substrate bonded to the first substrate based on a melting of the second substrate caused by heating of the portion of the electrical trace from an electrical current through the portion of the electrical trace from an electrical power source.

12. The device of claim 11, wherein the electrical trace defines a coil and is configured to electrically couple to the electrical power source via wireless inductive coupling.

13. The device of claim 11, wherein the second substrate comprises a liquid crystal polymer.

14. The device of claim 11, further comprising a plurality of electronic components, and wherein the electrical trace encircles the plurality of electronic components; and the second substrate is bonded to the first substrate and provides a hermetic seal around the plurality of electronic components.

15. The device of claim 11, further comprising a plurality of electronic components, and wherein the electrical trace individually and encircles at least two electronic components of the plurality of electronic components.

16. The device of claim 11, wherein the portion of the first substrate defines a cavity.

17. The device of claim 16, further comprising disposing a substance within the cavity.

18. The device of claim 16, wherein the first substrate has a plurality of portions, and wherein each portion of the first substrate defines a cavity, and wherein each cavity is encircled by an electrical trace and the second substrate hermetically seals each portion of the first substrate.

* * * * *